(12) United States Patent
Hamann et al.

(10) Patent No.: US 6,846,836 B2
(45) Date of Patent: Jan. 25, 2005

(54) N-SUBSTITUTED PHENYLUREA INHIBITORS OF MITOCHONDRIAL $F_1F_0$ ATP HYDROLASE

(75) Inventors: Lawrence G. Hamann, Cherry Hill, NJ (US); Andrew T. Pudzianowski, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/419,286

(22) Filed: Apr. 18, 2003

(65) Prior Publication Data

US 2004/0209821 A1 Oct. 21, 2004

(51) Int. Cl.$^7$ ............................................. A61K 31/445
(52) U.S. Cl. ...................................................... 514/317
(58) Field of Search ........................................ 514/317

(56) References Cited

U.S. PATENT DOCUMENTS

| | | |
|---|---|---|
| 5,610,144 A | 3/1997 | Capet et al. |
| 5,612,359 A | 3/1997 | Murugesan |
| 5,637,602 A | 6/1997 | Capet et al. |
| 5,712,279 A | 1/1998 | Biller et al. |
| 5,739,135 A | 4/1998 | Biller et al. |
| 5,760,246 A | 6/1998 | Biller et al. |
| 6,043,265 A | 3/2000 | Murugesan et al. |
| 6,194,437 B1 | 2/2001 | Horwell et al. |
| 6,423,689 B1 | 7/2002 | Booth et al. |
| 6,548,529 B1 | 4/2003 | Robl et al. |
| 2003/0022890 A1 | 1/2003 | Atwal et al. |

FOREIGN PATENT DOCUMENTS

| | | |
|---|---|---|
| JP | 2002173476 | 6/2002 |
| WO | WO 92/04045 | 3/1992 |
| WO | WO 93/01167 | 1/1993 |
| WO | WO 95/35314 | 12/1995 |
| WO | WO 99/65932 | 12/1999 |
| WO | WO 99/67221 | 12/1999 |
| WO | WO 00/01389 | 1/2000 |
| WO | WO 00/09543 | 2/2000 |

OTHER PUBLICATIONS

Moody, et al., European Journal of Pharmacology 409 (200) pp. 133–142.

Ashwood et al., Bioorganic & Medicinal Chemistry Letters 8 (1998) pp. 2589–2594.

Eden et al., Bioorganic & Medicinal Chemistry Letters, vol. 6, No. 21 pp. 2617–2622, no date available.

Ashwood, V. et al., "PD 176252—The First High Affinity Non–peptide Gastrin–Releasing Peptide ($BB_2$) Receptor Antagonist", Bioorganic & Medicinal Chemistry Letters, vol. 8, pp. 2589–2594 (1998).

Bundgaard, H., "(C) Means to Enhance Penetration: (1) Prodrugs as a means to improve the delivery of peptide drugs", Advanced Drug Delivery Reviews, vol. 8, pp. 1–38 (1992).

Cross, R.L. et al., "The Mode of Inhibition of Oxidative Phosphorylation by Efrapeptin (A23871): Evidence for an Alternating Site Mechanism for ATP Synthesis", The Journal of Biological Chemistry, vol. 253, No. 4, pp. 4865–4873 (1978).

Eden, J.M. et al., "PD 165929—The First High Affinity Non–peptide Neuromedin–B (NMB) Receptor Selective Antagonist", Bioorganic & Medicinal Chemistry Letters, vol. 6, No. 21, pp. 2617–2622 (1996).

Gasnier, F. et al., "Use of Percoll Gradients for Isolation of Human Placenta Mitochondria Suitable for Investigating Outer Membrane Proteins", Analytical Biochemistry, vol. 212, pp. 173–178 (1993).

Kakeya, N. et al., "Studies on Prodrugs of Cephalosporins. I. Synthesis and Biological Properties of Glycyloxybenzoyloxymethyl and Glycylaminobenzoyloxymethy Esters of 7 β–[2–(2–Aminothiazol–4–yl)–(Z)–2–methoxyiminoacet amido]–3–methyl–3–cephem–4–carboxylic Acid", Chem. Pharm. Bull., vol. 32, No. 2, pp. 692–698 (1984).

Matsuno–Yagi, A. et al., "Studies on the mechanism of oxidative phosphorylation: Effects of specific $F_0$ modifiers on ligand–induced conformation changes of $F_1$", Proc. Natl. Acad. Sci. USA, vol. 82, pp. 7550–7554 (1985).

Maughfling, E.J.R. et al., "Construction of chimeric human bombesin receptors to identify neuromedin B and gastrin–releasing peptide receptor binding sites", Biochemical Society Transactions, vol. 25, p. 455S (1997).

(List continued on next page.)

Primary Examiner—Raymond J. Henley, III
(74) Attorney, Agent, or Firm—Laurelee A. Duncan

(57) ABSTRACT

Compounds having the formula (I), are useful as inhibitors of mitochondrial $F_1F_0$ ATP hydrolase, wherein $R^1$–$R^8$, X, A, Z, n and m are defined herein.

21 Claims, No Drawings

OTHER PUBLICATIONS

Moody, T.W. et al., "Nonpeptide neuromedin B receptor antagonists inhibit the proliferation of C6 cells", European Journal of Pharmacology, vol. 409, pp. 133–142 (2000).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285–298 (1988).

Pullman, M.E. et al., "Partial Resolution of the Enzymes Catalyzing Oxidative Phosphorylation", The Journal of Biological Chemistry, vol. 235, No. 11, pp. 3322–3329 (1960).

Salomon, A.R. et al., "Understanding and exploiting the mechanistic basis for selectivity of polyketide inhibitors of $F_0F_1$–ATPase", PNAS, vol. 97, No. 26, pp. 14766–14771 (2000).

N-SUBSTITUTED PHENYLUREA INHIBITORS OF MITOCHONDRIAL $F_1F_0$ ATP HYDROLASE

FIELD OF THE INVENTION

This invention relates to N-substituted phenylurea compounds that inhibit mitochondrial $F_1F_0$ ATP hydrolase, and are therefore potentially useful for the treatment of a variety of ischemia-related diseases and disorders, including peripheral occlusive arterial disease, intermittent claudication, chronic stable angina pectoris, stroke, myocardial infarction

BACKGROUND OF THE INVENTION

Ischemic heart disease is a common and serious health problem. Every year, large numbers of patients die from ischemic heart disease and its complications. Many others experience acute myocardial infarcation, congestive heart failure, cardiac arrhythmias, or other disorders.

Myocardial ischemia exists when the heart tissue experiences a demand for oxygen and substrates that exceed the supply. Imbalances between oxygen supply and demand span a large range, and thus, there are various syndromes and biochemical pathways involved in the pathogenesis of ischemia, e.g., from low-grade to severe ischemic conditions. For example, chronic stable angina pectoris is a low-grade condition, in which the resting coronary blood flood may be normal but the blood flow reserve is insufficient to meet an increased energy demand. In more extreme situations, the ischemic muscle can develop an impaired contractile function and potential to generate arrhythmias. Major consequences of myocardial ischemia include mechanical and electrical dysfunction, muscle cell damage, and development of necrosis. Acute ischemic events may develop where there is coronary atherosclerosis. Ultimately, if the ischemia is sufficiently severe there will be an immediate reduction (or cessation) of contractile function in the heart.

The impairment of contractile function in ischemic muscle is associated with mitochondrial levels of adenosine triphosphate (ATP) and adenosine triphosphatases (ATPases). ATPases are enzymes that typically catalyze the hydrolysis of ATP, the main energy currency in cells, to adenosine monophosphate (AMP) or adenosine diphosphate (ADP), plus phosphate ions and energy. The contractile function of the heart is regulated by the transport of calcium, sodium, and potassium ions, which in turn is modulated by ATP and ATPases. More particularly, intracellular ATP is split by Na+, K+ ATPase, an enzyme that is responsible for maintaining a gradient of sodium and potassium ions across the cell membrane. The splitting of ATP by Na+, K+ ATPase releases the energy needed to transport K+ and Na+ ions against concentration gradients. This enables the existence of a resting potential in the membrane (i.e, Na+ out, K+ in) which initiates the contractile response. Contraction is triggered by Na/Ca exchange and $Ca^{2+}$ transport, the energy for which is generated by the hydrolysis of ATP by $Ca^{2+}$ ATPase.

To maintain homeostasis, the cells' supply of ATP must be replenished as it is consumed (e.g., with muscle contraction). During the steady state, the rate of ATP synthesis needs to be closely matched to its rate of consumption. Arguably, the most important ATPase is the mitochondrial $F_1F_0$-ATPase. Unlike other ATPases which function typically to hydrolyze ATP and release energy, the $F_1F_0$-ATPase has both hydrolytic and synthetic states. As "ATP synthase", the mitochondrial $F_1F_0$-ATPase catalyzes the production of ATP via oxidative phosphorylation of ADP and $P_i$. Thus, $F_1F_0$-ATPase is responsible for producing the cell's main energy source, ATP. In normoxic conditions, mitochondrial $F_1F_0$-ATPase modulates this ATP production via its two units, the $F_1$ and $F_0$ complexes. $F_0$ is the inner membrane domain, and $F_1$ is a catalytic domain consisting of five subunits ($\alpha\beta\chi\delta\epsilon$—the catalytic site is on the $\beta$ unit), that protrude from the $F_0$ domain into the mitochondrial matrix. When sufficient levels of oxygen are present, electrons from ATPase substrates are transferred to oxygen, and protons are transported out of the mithcondrial matrix. This proton/electron transport creates an electrochemical proton gradient across the mitochondrial membrane and through the $F_0$ domain which drives the $F_1$ domain to synthesize ATP.

In ischemic conditions, however, this electrochemical gradient collapses, and $F_1F_0$-ATPase switches to its hydrolytic state. This hydrolysis of ATP seems to serve no useful purpose. Also, as $F_1F_0$-ATPase operates in its hydrolytic state there is a down-regulation of $F_1F_0$-ATP synthase. $F_1F_0$-ATP synthase activities in vesicles from ischemic muscle typically are substantially (up to ~50–80%) less than those of control muscle. A native peptide called $IF_1$ inhibitor protein (or $IF_1$) may be bound to the $F_1$ unit under ischemic conditions to inhibit the ATP hydrolase activity of the enzyme; however, $IF_1$ is highly pH dependent and in severe conditions can provide only a modicum of control. The conversion of $F_1F_0$-ATP synthase to $F_1F_0$-ATP hydrolase is reversible, as addition of substrate and oxygen to the mitochondria of ischemic muscle can reactivate the $F_1F_0$-ATPase and ATP levels to control levels.

As may be appreciated, in ischemic conditions the activity of $F_1F_0$-ATPase produces a futile cycling and waste of ATP. It is believed that this depletion of ATP and/or ATP synthase may suppress the Na+K+ pump to increase cardiac contractility, vasoconstriction, sensitivity to vasoactive agents, and arterial blood pressure. Several inhibitors of $F_1F_0$-ATPase have been described, including efrapeptin, oligomycin, autovertin B, and azide. Oligomycin targets $F_0$ and reportedly postpones cell injury by preserving ATP during ischemia. However, the only known inhibitors of $F_1F_0$-ATPase are large proteins or peptides which are not orally bioavailable.

Accordingly, there is an ongoing need for useful inhibitors of $F_1F_0$-ATPase inhibitors, especially those that are orally bioavailable.

SUMMARY OF THE INVENTION

In accordance with the present invention, a method of treating a mitochondrial $F_1F_0$ ATP hydrolase associated disorder in a mammal is described comprising administering to the patient in need of such treatment an effective amount of at least one compound having the formula (I):

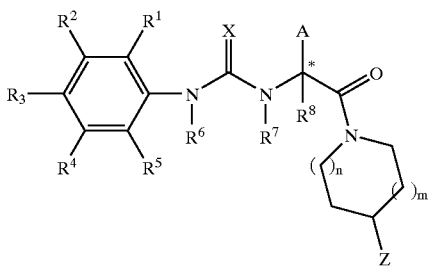

(I)

their enantiomers, diastereomers, and pharmaceutically acceptable salts, prodrugs and solvates thereof, wherein:

X is selected from O or S;

A is selected from hydrogen, alkyl, substituted alkyl, cycloalkyl, heterocycle, aryl, and heteroaryl;

n and m are 0, 1, or 2

$R^1$ through $R^5$ are independently selected from hydrogen, halogen, $NO_2$, CN, $C_{1-8}$alkyl, substituted $C_{1-8}$alkyl, $C_{3-8}$cycloalkyl, aryl, heterocyclo, heteroaryl, $OR^9$, $SR^9$, $COR^{11}$, $CO_2R^{11}$, $CONR^9R^{10}$ or $NR^9R^{10}$;

$R^6$ and $R^7$ are independently hydrogen, alkyl or substituted alkyl;

$R^8$ is hydrogen; $C_{1-8}$alkyl, substituted $C_{1-8}$alkyl, aryl, heterocyclo or heteroaryl;

Z is hydrogen, alkyl, substituted alkyl, cycloalkyl, aryl, heterocyclo, heteroaryl, $COR^{11}$, $CO_2R^{11}$, $SO_2R^{11}$, $S(O)R^{11}$ or $CONR^9R^{10}$;

$R^9$ and $R^{10}$ are independently hydrogen, $C_{1-8}$alkyl, substituted $C_{1-8}$alkyl, $C_{3-10}$cycloalkyl, aryl, heterocyclo, heteroaryl, $COR^{13}$, $SO_2R^{13}$ or $S(O)R^{13}$; and $R^{11}$, $R^{12}$ and $R^{13}$ are independently hydrogen, $C_{1-8}$alkyl, substituted $C_{1-8}$alkyl, $C_{3-10}$cycloalkyl, aryl, heterocyclo or heteroaryl;

wherein each occurrence of $R^9$–$R^{13}$ is chosen independently.

DETAILED DESCRIPTION

The instant invention provides N-substituted phenylurea compounds that are potent and selective inhibitors of $F_1F_0$-ATP hydrolase. The compounds of the present invention are useful in treating or preventing conditions associated with ischemia, particularly myocardial ischemia and associated conditions, such as muscle cell damage, necrosis, and cardiac arrhythmias. Also, in view of their inhibitory activity, the inventive compounds may be used to treat cancer and tumor growth.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms. The expression "lower alkyl" refers to unsubstituted alkyl groups of 1 to 4 carbon atoms.

The term "substituted alkyl" refers to an alkyl group as defined above having one, two, three, or four substituents selected from the group consisting of halogen, trifluoromethyl, alkenyl, alkynyl, nitro, cyano, keto (=O), $OR_a$, $SR_a$, $NR_aR_b$, $NR_aSO_2$, $NR_aSO_2R_c$, $SO_2R_c$, $SO_2NR_aR_b$, $CO_2R_a$, $C(=O)R_a$, $C(=O)NR_aR_b$, $OC(=O)R_a$, $-OC(=O)NR_aR_b$, $NR_aC(=O)R_b$, $NR_aCO_2R_b$, =N—OH, =N—O-alkyl, aryl, heteroaryl, heterocyclo and cycloalkyl, wherein $R_a$ and $R_b$ are selected from hydrogen, alkyl, alkenyl, cycloalkyl, heterocyclo, aryl, and heteroaryl, and $R_c$ is selected from hydrogen, alkyl, cycloalkyl, heterocyclo aryl and heteroaryl. When a substituted alkyl includes an aryl, heterocyclo, heteroaryl, or cycloalkyl substituent, said ringed systems are as defined below and thus may in turn have zero to four substituents (preferably 0–2 substituents), also as defined below. When either $R_a$, $R_b$ or $R_c$ is an alkyl or alkenyl, said alkyl or alkenyl may optionally be substituted with 1–2 of halogen, trifluoromethyl, nitro, cyano, keto (=O), OH, O(alkyl), phenyloxy, benzyloxy, SH, S(alkyl), $NH_2$, NH(alkyl), N(alkyl)$_2$, $NHSO_2$, $NHSO_2$(alkyl), $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, —OC(=O)NH(alkyl), NHC(=O)alkyl, and/or $NHCO_2$(alkyl).

"Alkyl" when used in conjunction with another group such as in arylalkyl refers to a substituted alkyl in which at least one of the substituents is the specifically-named group. For example, the term arylalkyl includes benzyl, or any other straight or branched chain alkyl having at least one aryl group attached at any point of the alkyl chain.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

When reference is made to a substituted alkylene, alkenylene, or alkynylene group, these groups are substituted with one to four substitutents as defined above for alkyl groups. A substituted alkylene, alkenylene, or alkynylene may have a ringed substituent attached in a spiro fashion.

The term "alkoxy" refers to an alkyl, alkenyl, or substituted alkyl or alkenyl group bonded through an oxygen atom (—O—). For example, the term "alkoxy" includes the groups —O—$C_{1-12}$alkyl, —O—$C_{2-8}$alkenyl, and so forth.

The term "alkylthio" refers to an alkyl or alkenyl or substituted alkyl or alkenyl group bonded through a sulfur (—S—) atom. For example, the term "alkylthio" includes the groups —S—$(CH_2)CH_3$, —S—$CH_2$aryl, etc.

The term "alkylamino" refers to an alkyl or alkenyl or substituted alkyl or alkenyl group bonded through a nitrogen (—NR'—) group. For example, the term "aminoalkyl"

includes the groups —NR'—$C_{1-2}$alkyl and —NR'—$CH_2$-aryl, etc. (where R' is hydrogen, alkyl or substituted alkyl as defined above.) "Amino" refers to the group —$NH_2$.

When a subscript is used, as in $C_{1-8}$alkyl, the subscript refers to the number of carbon atoms the group may contain. Zero when used in a subscript denotes a bond, e.g., $C_{0-4}$alkyl refers to a bond or an alkyl of 1 to 4 carbon atoms. When used with alkoxy, thioalkyl, or alkylamino (or aminoalkyl), a subscript refers to the number of carbon atoms that the group may contain in addition to heteroatoms. Thus, for example, monovalent $C_{1-2}$alkylamino includes the groups —NH—$CH_3$, —NH—$CH_2$—$CH_3$, and —N—$(CH_3)_2$. A lower aminoalkyl comprises an aminoalkyl having one to four carbon atoms.

The alkoxy, thioalkyl, or aminoalkyl groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—$C_{1-12}$alkyl, whereas a bivalent alkoxy includes groups such as —O—$C_{1-12}$alkylene-, etc.

The term "acyl" refers to a carbonyl

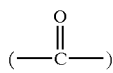

linked to an organic group i.e.,

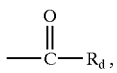

wherein $R_d$ may be selected from alkyl, alkenyl, substituted alkyl, substituted alkenyl, aryl, heterocyclo, cycloalkyl, or heteroaryl, as defined herein.

The term "alkoxycarbonyl" refers to a group having

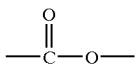

linked to an organic radical, $R_d$, i.e.,

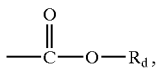

wherein $R_d$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "sulfonyl" refers to a sulphoxide group (i.e., —$S(O)_{1-2}$) linked to an organic radical $R_c$, as defined above.

The term "sulfonamidyl" or "sulfonamido" refers to the group —$S(O)_2NR_eR_f$, wherein $R_e$ and $R_f$ are as defined above. Preferably when one of $R_e$ and $R_f$ is optionally substituted heteroaryl or heterocycle (as defined below), the other of $R_e$ and $R_f$ is hydrogen, alkyl, or substituted alkenyl.

The term "cycloalkyl" refers to fully saturated and partially unsaturated hydrocarbon rings of 3 to 9, preferably 3 to 7 carbon atoms. The term "cycloalkyl" includes such rings having zero to four substituents (preferably 0–2 substituents), selected from the group consisting of halogen, alkyl, substituted alkyl (e.g., trifluoromethyl), alkenyl, substituted alkenyl, alkynyl, nitro, cyano, keto, $OR_d$, $SR_d$, $NR_dR_e$, $NR_cSO_2$, $NR_cSO_2R_c$, C(=O)H, acyl, —$CO_2H$, alkoxycarbonyl, carbamyl, sulfonyl, sulfonamide, —OC(=O)$R_d$, =N—OH, =N—O-alkyl, aryl, heteroaryl, heterocyclo, a 4 to 7 membered carbocyclic ring, and a five or six membered ketal, e.g., 1,3-dioxolane or 1,3-dioxane, wherein $R_c$, $R_d$ and $R_e$ are defined as above. The term "cycloalkyl" also includes such rings having a phenyl ring fused thereto or having a carbon-carbon bridge of 3 to 4 carbon atoms. Additionally, when a cycloalkyl is substituted with a further ring, i.e., aryl, arylalkyl, heteroaryl, heteroarylalkyl, heterocyclo, heterocycloalkyl, cycloalkylalkyl, or a further cycloalkyl ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), N(alkyl)$_2$, $NHSO_2$, $NHSO_2$(alkyl), $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, —OC(=O)NH(alkyl), NHC(=O)alkyl, and $NHCO_2$(alkyl).

The term "aryl" refers to phenyl, biphenyl, 1-naphthyl, 2-naphthyl, and anthracenyl, with phenyl being preferred. The term "aryl" includes such rings having zero to four substituents (preferably 0–2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2$, $NR_dSO_2R_c$, C(=O)H, acyl, —$CO_2H$, alkoxycarbonyl, carbamyl, sulfonyl, sulfonamide, —OC(=O)$R_d$, heteroaryl, heterocyclo, cycloalkyl, phenyl, benzyl, napthyl, including phenylethyl, phenyloxy, and phenylthio, wherein $R_c$, $R_d$ and $R_e$ are defined as above. Additionally, two substituents attached to an aryl, particularly a phenyl group, may join to form a further ring such as a fused or spiro-ring, e.g., cyclopentyl or cyclohexyl or fused heterocycle or heteroaryl. When an aryl is substituted with a further ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), N(alkyl)$_2$, $NHSO_2$, $NHSO_2$(alkyl), $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, —OC(=O)NH(alkyl), NHC(=O)alkyl, and $NHCO_2$(alkyl).

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to four substituents (preferably 0–2 substituents), selected from the group consisting of halo, alkyl, substituted alkyl (e.g., trifluoromethyl), alkenyl, substituted alkenyl, alkynyl, nitro, cyano, keto, $OR_d$, $SR_d$, $NR_dR_e$, $NR_dSO_2$, $NR_dSO_2R_c$, $SO_2R_d$, C(=O)H, acyl, —CO$_2$H, alkoxycarbonyl, carbamyl, sulfonyl, sulfonamide, —OC(=O)$R_d$, =N—OH, =N—O-alkyl, aryl, heteroaryl, cycloalkyl, a five or six membered ketal, e.g., 1,3-dioxolane or 1,3-dioxane, or a monocyclic 4 to 7 membered non-aromatic ring having one to four heteroatoms, wherein $R_c$, $R_d$ and $R_e$ are defined as above. The term "heterocyclo" also includes such rings having a phenyl ring fused thereto or having a carbon-carbon bridge of 3 to 4 carbon atoms. Additionally, when a heterocyclo is substituted with a further ring, i.e., aryl, arylalkyl, heteroaryl, heteroarylalkyl, cycloalkyl, cycloalkylalkyl, heterocycloalkyl, or a further heterocyclo ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl), SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH(alkyl), NHC(=O)alkyl, and NHCO$_2$(alkyl).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero to four substituents (preferably 0–2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2$, $NR_dSO_2R_c$, $SO_2R_d$, C(=O)H, acyl, —CO$_2$H, alkoxycarbonyl, carbamyl, sulfonyl, sulfonamide, —OC(=O)$R_d$, heterocyclo, cycloalkyl, aryl, or a monocyclic 4 to 7 membered aromatic ring having one to four heteroatoms, including phenylethyl, phenyloxy, and phenylthio, wherein $R_c$, $R_d$ and $R_e$ are defined as above. Additionally, when a heteroaryl is substituted with a further ring, i.e., aryl, arylalkyl, heterocyclo, heterocycloalkyl, cycloalkyl, cycloalkylalkyl, heteroarylalkyl, or a further heteroaryl ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), NH$_2$, NH(alkyl), N(alkyl)$_2$, NHSO$_2$, NHSO$_2$(alkyl),n SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH(alkyl), NHC(=O)alkyl, and NHCO$_2$(alkyl).

Exemplary monocyclic heteroaryl groups include pyrrolyl, pyrazolyl, pyrazolinyl, imidazolyl, oxazolyl, isoxazolyl, thiazolyl (i.e., (i.e., 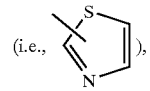), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds. The phrase "optionally substituted" is intended to include substituted or unsubstituted possibilities. Accordingly, the phrase "each group of which may be optionally substituted means that each group includes both substituted and unsubstituted groups.

The use of the phrase "where valence allows" means that the groups may be substituted only to the degree and nature allowed by valency of the group. This is commonly understood by those of skill in the art. For example, a hydrogen substituent cannot be further substituted nor can a phenyl group be directly substituted by an oxo group due to limits on valency.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

The compounds of formula I which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asymmetric carbons) and diastereomeric forms, are contemplated within and the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

In addition, compounds of the formulas I may have prodrug forms. Any compound that will be converted in vivo to provide the bioactive agent (i.e., a compound of formula I) is a prodrug within the scope and spirit of the invention.

For example, pro-drug compounds of the formulas I may be carboxylate ester moieties. A carboxylate ester may be conveniently formed by esterifying any of the carboxylic acid functionalities found on the disclosed ring structure(s).

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et. al. (Academic Press, 1985).

b) *A Textbook of Drug Design and Development*, edited by Krosgaard-Larsen and H. Bundgaard, Chapter 5, "Design and Application of Prodrugs," by H. Bundgaard, p. 113–191 (1991).

c) H. Bundgaard, *Advanced Drug Delivery Reviews*, 8, 1–38 (1992).

d) H. Bundgaard, et. al., *Journal of Pharmaceutical Sciences*, 77, 285 (1988).

e) N. Kakeya, et. al., *Chem Phar Bull*, 32, 692 (1984).

It should further be understood that solvates (e.g., hydrates) of the compounds of formulas I–IV are also with the scope of the present invention. Methods of solvation are generally known in the art.

Preferred Methods

Preferred methods of the present invention are those in which the method comprises administering an effective amount of a compound of formula (I) (above), their enantiomers, diastereomers, and pharmaceutically acceptable salts, prodrugs and solvates thereof, in which $R^2$, $R^3$ and $R^4$ are all hydrogen; and/or $R^6$ and $R^7$ are both hydrogen; and/or n and m are both 1; and/or $R^1$ and $R^5$ are both $C_{1-8}$alkyl, preferably both $R^1$ and $R^5$ are isopropyl groups.

Other preferred methods include the administration of at least one compound of formula (I), their enantiomers, diastereomers, and pharmaceutically acceptable salts, prodrugs and solvates thereof, in which Z is $C_{1-8}$alkyl, $C_{2-8}$alkenyl, $C_{1-8}$haloalkyl, cycloalkyl, aryl, arylalkyl, heteroaryl, heteroarylalkyl —$COR^{11}$, —$CO_2R^{11}$, —$SO_2R^{11}$, —$S(O)R^{11}$ or —$CONR^9R^{10}$; especially preferable is benzyl, —$C(O)_2H$ or —$C(O)_2C_{1-8}$alkyl;

$R^9$ is hydrogen;

$R^{10}$ is $C_{1-8}$alkyl or $C_{3-10}$cycloalkyl; aryl or arylalkyl; and $R^{11}$ is hydrogen, $C_{1-8}$alkyl, $C_{3-10}$cycloalkyl, $C_{3-10}$heterocycloalkyl, $C_{3-10}$aryl or $C_{3-10}$arylalkyl.

Another preferred method within the scope of formula (I), comprises the administration of compounds of formula (I), their enantiomers, diastereomers, and pharmaceutically acceptable salts, prodrugs and solvates thereof, in which A is hydrogen, $C_{1-8}$alkyl, heteroaryl, aryl, or alkyl substituted with heterocyclo, aryl, OH, SH, $ST^1$, —$C(O)_tH$, $T^3$-$NT^5T^6$, -$T^8$-$C(O)_tT^9$-$NT^5T^6$ or $T^3$-$N(T^2)T^4NT^5T^6$, $T^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^2$ and $T^3$ are each independently a single bond, -$T^8$-S(O)$_t$-$T^9$-, -$T^8$-C(O)-$T^9$-, -$T^{18}$-C(S)-$T^9$-, -$T^8$-O-$T^9$-, -$T^8$-S-$T^9$-, -$T^8$-O—C(O)-$T^9$-, -$T^8$-C(O)$_t$$T^9$-, -$T^8$-C(=$NT^{10}$)-$T^9$- or -$T^8$-C(O)—C(O)-$T^9$-;

$T^5$, $T^6$, $T^7$, $T^8$ and $T^9$ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —OT$^{11}$, —ST$^{11}$, —C(O)$_t$H, —C(O)$_t$T$^{11}$, —O—C(O)T$^{11}$, T$^8$C(O)$_t$N(T$^{12}$)T$^{11}$, —SO$_3$H, —S(O)$_t$T$^{11}$, S(O)$_t$N(T$^{12}$)T$^{11}$, —T$^{13}$-NT$^{11}$T$^{12}$, -T$^{13}$—N(T$^{12}$)-T$^4$-NT$^{11}$T$^{22}$, -T$^{13}$-N(T$^{11}$)-T$^{12}$-T$^{11}$ and -T$^{13}$-N(T$^{18}$)-T$^{14}$-H; or T$^8$ and T$^9$ are each independently a single bond, alkylene, alkenylene or alkynylene;

T$^{11}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

T$^{12}$ is halo, cyano, nitro, OH, oxo, —SH, alkyl, (hydroxy) alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, —C(O)$_t$H or —SO$_3$H;

T$^{13}$ and T$^{14}$ are each independently a single bond, —S(O)$_t$—, —C(O)—, —C(S)—, —O—, —S—, —O—C(O)—, —C(O)$_t$—, —C(=NT$^{13}$)— or —C(O)—C(O)—;

wherein each occurrence of T$^1$–T$^{14}$ is chosen independently; and t is 1 or 2.

Preferred compounds of the foregoing method are those in which A is hydrogen, C$_{1-8}$alkyl, hydroxyalkyl, heterocycloalkyl, heteroaryl alkyl, aryl, arylalkyl, or alkyl substituted with a group selected from SH, ST$^4$, —C(O)$_t$H, T$^6$-NT$^8$T$^9$, -T$^{11}$-C(O)$_t$T$^{12}$-NT$^8$T$^9$ and T$^6$-N(T$^5$)T$^7$NT$^8$T$^9$. More preferred are those compounds in which A is hydrogen, methyl, —CH$_2$(CH$_3$)$_2$, —(CH$_2$)$_2$(CH$_3$)$_2$, —CH(CH$_3$)CH$_2$(CH$_3$), —(CH$_2$)OH, hydroxyethyl, —(CH$_2$)$_2$SCH$_3$, —CH$_2$SH, phenyl, —CH$_2$(phenyl), —CH$_2$(p-hydroxyphenyl), —CH$_2$(indole), —(CH$_2$)C(O)NH$_2$, —(CH$_2$)$_2$C(O)NH$_2$, —(CH$_2$)$_2$C(O)OH, —CH$_2$C(O)OH, —(CH$_2$)$_4$NH$_2$, —(CH$_2$)$_3$(=NH)CNH$_2$, or —CH$_2$(imidazole). Especially preferred A groups are —CH(CH$_3$) CH$_2$(CH$_3$), phenyl, phenyl alkyl or —CH$_2$(2-indole).

Alternatively preferred methods of treating mitochondrial F$_1$F$_0$ ATP hydrolase associated disorders in a mammal comprise administering to the patient in need of such treatment an effective amount of at least one compound having the formula (II):

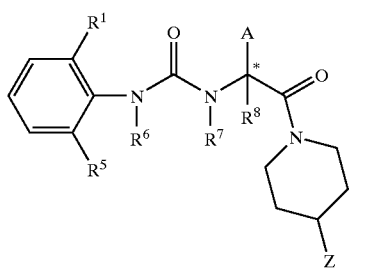

(II)

their enantiomers, diastereomers, and pharmaceutically acceptable salts, prodrugs and solvates thereof, wherein:

A is hydrogen, C$_{1-8}$alkyl, heteroaryl, aryl, or alkyl substituted with heterocyclo, aryl, OH, SH, ST$^1$, —C(O)$_t$H, T$^3$-NT$^5$T$^6$, -T$^8$-C(O)$_t$T$^9$-NT$^5$T$^6$ or T$^3$-N(T$^2$)T$^4$NT$^5$T$^6$;

R$^1$ and R$^5$ are independently C$_{1-8}$alkyl optionally substituted where valence allows;

R$^6$ and R$^7$ are independently hydrogen or C$_{1-8}$alkyl;

R$^8$ is hydrogen, C$_{1-8}$alkyl or substituted C$_{1-8}$alkyl;

Z is hydrogen, C$_{1-8}$alkyl, C$_{2-8}$alkenyl, C$_{1-8}$haloalkyl, cycloalkyl, aryl, arylalkyl, heteroaryl, heteroarylalkyl —COR$^{11}$, —CO$_2$R$^{11}$, —SO$_2$R$^{11}$, —S(O)R$^{11}$ or —CONR$^9$R$^{10}$;

R$^9$ is hydrogen,

R$^{10}$ is C$_{1-8}$alkyl or C$_{3-10}$cycloalkyl; aryl or arylalkyl;

R$^{11}$ is hydrogen, C$_{1-8}$alkyl, C$_{3-10}$cycloalkyl, C$_{3-10}$heterocycloalkyl, C$_{3-10}$aryl or C$_{3-10}$arylalkyl.

T$^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

T$^2$ and T$^3$ are each independently a single bond, -T$^8$-S(O)$_t$-T$^9$-, -T$^8$-C(O)-T$^9$-, -T$^{18}$-C(S)-T$^9$-, -T$^8$-O-T$^9$-, -T$^8$-S-T$^9$-, -T$^8$-O—C(O)-T$^9$-, -T$^8$-C(O)$_t$T$^9$-, -T$^8$-C(=NT$^{10}$)-T$^9$- or -T$^8$-C(O)—C(O)-T$^9$-;

T$^5$, T$^6$, T$^7$, T$^8$ and T$^9$ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —OT$^{11}$, —ST$^{11}$, —C(O)$_t$H, —C(O)$_t$T$^{11}$, —O—C(O)T$^{11}$, T$^8$C(O)$_t$N(T$^{12}$)T$^{11}$, —SO$_3$H, —S(O)$_t$T$^{11}$, S(O)$_t$N(T$^{12}$)T$^{11}$, -T$^{13}$-NT$^{11}$T$^{12}$, -T$^{13}$-N(T$^{12}$)-T$^4$-NT$^{11}$T$^{22}$, -T$^{13}$-N(T$^{11}$)-T$^{12}$-T$^{11}$ and -T$^{13}$-N(T$^{18}$)-T$^{14}$-H; or T$^8$ and T$^9$ are each independently a single bond, alkylene, alkenylene or alkynylene;

T$^{11}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

T$^{12}$ is halo, cyano, nitro, OH, oxo, —SH, alkyl, (hydroxy) alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —C(O)$_t$H or —SO$_3$H;

T$^{13}$ and T$^{14}$ are each independently a single bond, —S(O)$_t$—, —C(O)—, —C(S)—, —O—, —S—, —O—C(O)—, —C(O)$_t$—, —C(=NT$^{13}$)- or —C(O)—C(O)—; and t is 1 or 2.

More preferred methods comprise administering at least one compound of formula (II) (above), their enantiomers, diastereomers, and pharmaceutically acceptable salts, prodrugs and solvates thereof, in which A is hydrogen, methyl, —CH$_2$(CH$_3$)$_2$, —(CH$_2$)$_2$(CH$_3$)$_2$, —CH(CH$_3$)CH$_2$(CH$_3$), —(CH$_2$)OH, hydroxyethyl, —(CH$_2$)$_2$SCH$_3$, —CH$_2$SH, phenyl, —CH$_2$(phenyl), —CH$_2$(p-hydroxyphenyl), —CH$_2$(indole), —(CH$_2$)C(O)NH$_2$, —(CH$_2$)$_2$C(O)NH$_2$, —(CH$_2$)$_2$C(O)OH, —CH$_2$C(O)OH, —(CH$_2$)$_4$NH$_2$, —(CH$_2$)$_3$(=NH)CNH$_2$ or —CH$_2$(imidazole). Especially preferred are methods comprising administering at least one compound of formula (II), their enantiomers, diastereomers, and pharmaceutically acceptable salts, prodrugs and solvates thereof, in which A is —CH(CH$_3$)CH$_2$(CH$_3$), phenyl, CH$_2$(phenyl) or —CH$_2$(2-indole). Also especially preferred methods within the scope of formula (II) are those compounds, their diastereomers and pharmaceutically acceptable salts, prodrugs and solvates thereof, wherein $R^8$ is hydrogen and the configuration about the carbon marked with the * is S, provided A is not H.

Other preferred methods comprise administering at least one compound of formula (II), their enantiomers, diastereomers, and pharmaceutically acceptable salts, prodrugs and solvates thereof, in which $R^1$ and $R^5$ are both isopropyl; and/or $R^6R^7$ and $R^9$ are all hydrogen; and/or Z is $CH_2$(phenyl), $—C(O)_2H$ or $—C(O)_2C_{1-8}$alkyl.

Utility

The compounds of this invention by inhibiting $F_1F_0$-ATPase may be used to help conserve ATP under conditions of oxygen deprivation. Thus, the compounds may be useful in treating or preventing any condition associated with depleted levels of ATP and/or tissue ischemia (from mild to acute or severe). As used herein with reference to the utilities described below, the terms "treating" or "treatment" encompass both responsive and prophylaxis measures designed to inhibit or delay the onset of the disease or disorder, or to alleviate, ameliorate, lessen, or cure the disease or disorder and/or its symptoms.

In view of their $F_1F_0$-ATPase inhibitory activity, the inventive compounds are useful in treating cardiovascular diseases including, without limitation, congestive heart failure, cardiac arrhythmias, unstable angina, and high blood pressure. The compounds also are useful to treat ischemia, including ischemia resulting from vascular occlusion, cerebral infarction, stroke and related cerebral vascular diseases (including cerebrovascular accident and transient ischemic attack), and accurate coronary syndromes such as myocardial infarction, coronary artery disease, unstable angina, and non-Q wave MI.

Additionally, the compounds are useful in treating or preventing symptoms or consequences occurring from thrombosis and/or the formation of atherosclerotic plaques, atherosclerosis, peripheral arterial disease, coagulation syndromes, and intermittent claudication. The compounds may be used to treat thrombotic or thromboembolic conditions such as thromboembolic stroke (including that resulting from atrial fibrillation or from ventricular mural thrombus); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequenses of medication (such as oral contraceptives, hormome replacement and heparin); thrombotic consequenses of atherosclerotic vascular disease and atherosclerotic plaque rupture leading to tissue ischemia; prevention of atherosclerotic plaque formation; transplant atherosclerosis; thromboembolic complications of pregancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation); coagulation syndromes; vascular remodeling atherosclerosis, restenosis and systemic infection; prevention of metastesis and tumor implantation; diabetic complications including retinopathy, nephropathy and neuropathy; inflammation; Kasabach-Merritt syndrome; atrial fibrillation; ventricular enlargement (including dilated cardiac myopathy and heart failure); restenosis (e.g., following arterial injury-induced either endogenously or exogenously).

Compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation. Additionally, the compounds may be used for preservation of tissue as related to organ transplantation.

The inventive compounds also are useful in treating diseases or disorders in other tissues or muscles that are associated with ischemic conditions. For example, the compounds may be used to treat muscle cell damage and necrosis.

Additionally, the inventive compounds may be useful as anti-cancer and/or anti-tumor agents. It is reported that inhibitors of mitochondrial $F_1F_0$-ATPase selectively kill metabolically active tumor cells that do not exhibit the Warburg effect, i.e., cells that do not maintain a high level of anaerobic carbon metabolism even in the presence of oxygen. See Salomon et al., "*Understanding and Exploiting the Mechanistic Basis for Selectivity of Polyketide Inhibitors of $F_1F_1$-ATPase,*" *Proc. Natl. Acad. Sci.* Vol. 97 (26) (2000), at pp. 14766–14771. Accordingly, the compounds of the present invention are useful in treating tumor growth, as an adjunct to chemotherapy, and for treating cancer, more particularly, cancer of the lung, prostate, colon, breast, ovaries, and bone.

The inventive compounds may also be used in combination with other $F_1F_0$-ATPase inhibitors such as efrapeptin, oligomycin, autovertin B, and azide, and/or in combination with other cardiovascular drugs. Additionally, the compounds may be used in combination with other therapeutic agents such as potassium channel openers, calcium channel blockers, sodium hydrogen exchanger inhibitors, anti-arrhythmic agents, thrombin inhibitors, platelet aggregation inhibitors or anti-platelet agents, fibrinogen antagonists, diuretics, anti-hypertensive agents, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-oxidant agents; angiogenesis modulators; anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

For example, the inventive compounds may be used in combination with aspirin, clopidogrel, ticlopidine or CS-747, warfarin, and low molecular weight heparins (such as lovenox, enoxaparain, and dalteparin). Other suitable therapeutic agents in combination with which the inventive compounds may be used include:

anti-arrhythmic agents including Class I agents (such as propafenone); Class II agents (propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in U.S. application Ser. No. 09/729,731, filed Dec. 5, 2000;

alpha- or beta-adrenergic blockers (such as propranolol, nadolol and carvedilol), or -(β-adrenergic agonists such as albuterol, terbutaline, formoterol, salmeterol, bitolterol, pilbuterol, and/or fenoterol;

angiotensin-II receptor antagonists (e.g., irbesartan, losartan or valsartan);

anticholinergics such as ipratropium bromide;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DPP4) inhibitors;

anti-depressant or anti-anxiety agents such as nefazodone, sertraline, diazepam, lorazepam, buspirone, and hydroxyzine pamoate;

anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;

anti-hypertensive agents such as angiotensin-converting enzyme (ACE) inhibitors (e.g., captopril, lisinopril, zofenopril, ramipril, fosinopril, enalapril, ceranopril, cilazopril, delapril, pentopril, quinapril), vasopeptidase inhibitors, i.e., dual ACE/NEP inhibitors (e.g., omapatrilat and gemopatrilat), AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors;

anti-inflammatory agents such as cromolyn, nedocromil, theophylline, zileuton, zafirlukast, monteleukast and/or pranleukast or cortiocosteroids including beclomethasone, triamcinolone, budesonide, fluticasone, flunisolide or dexamethasone; prednisone; dexamethasone; enbrel; protien tyrosine kinase (PTK) inhibitors; cyclooxygenase inhibitors (including NSAIDs, and COX-1 and/or COX-2 inhibitors); aspirin; or indomethacin; lipoxygenase inhibitors; chemokine receptor modulators (including CCR1, CCR2, CCR3, CXCR2 receptor antagonists); secretory and cytosolic phospholipase A2 inhibitors; VLA4 antagonists; cytokine modulators (e.g. TNF-alpha converting enzyme (TACE) inhibitors, Interleukin-1 converting enzyme (ICE) inhibitors, Interleukin-1 receptor antagonists);

angiogenesis modulators such as endostatin;

anti-oxidant agents and/or lipid peroxidation inhibitors such as probucol, BO-653, Vitamin A, Vitamin E, AGI-1067;

anti-platelet agents such as GPIIb/GPIIIa blockers, (e.g., abciximab, eptifibatide, tirofiban); $P2Y_{12}$ antagonists (e.g., clopidogrel, ticlopidine, CS-747); or thromboxane receptor antagonists (e.g., ifetroban);

anti-osteoporosis agents including alendronate and raloxifene.

anti-obesity agents including orlistat and aP2 inhibitors (such as those disclosed in U.S. Ser. No. 09/519,079 filed Mar. 6, 2000);

anti-proliferative agents for use in combination with the compounds of the present invention include cyclosporin A, paclitaxel, FK 506, and adriamycin;

anti-ulcer and gastroesophageal reflux disease agents including famotidine, ranitidine, and omeprazole;

sodium hydrogen exchanger-1 (NHE-1) inhibitors such as cariporide;

calcium channel blocking agents such as verapamil, nifedipine, diltiazem, amlodipine and mybefradil;

cardiac glycosides such as digitalis and ouabain;

diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride;

hormone replacement therapies including estrogen (e.g., congugated estrogens) and estradiol;

lipid profile modulators including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, or atavastatin or visastatin)); squalene synthetase inhibitors; fibrates; bile acid sequestrants (such as questran); ACAT1 inhibitors; ACAT2 inhibitors; dual ACAT1/2 inhibitors; MTP inhibitors; cholesterol absorption inhibitors; and cholesterol ester transfer protein inhibitors (e.g., CP-529414); PPAR-delta agonists; PPAR-alpha agonists; dual PPAR-alpha/delta agonists; LXR-alpha agonists; LXR-beta agonists; LXR dual alpha/beta agonists;

mineralocorticoid receptor antagonists such as spironolactone and eplirinone.

microsomal triglyceride transport protein inhibitors (such as disclosed in U.S. Pat. Nos. 5,739,135, 5,712,279 and 5,760,246);

phosphodiesterase (PDE) inhibitors including dipyridamole, cilostazol, or sildenafil, or PDE inhibitors in combination with aspirin, ifetroban, picotamide, ketanserin, clopidogrel, and/or thromboxane receptor antagonists or thromboxane A synthetase inhibitors (such as picotamide);

serotonin-2-receptor antagonists (such as ketanserin), fibrinogen receptor antagonists, and thrombolytic agents, such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), factor VIIa inhibitors, factor Xa inhibitors, thrombin inhibitors (such as hirudin and argatroban), animal salivary gland plasminogen activators, PAI-1 inhibitors such as XR-330 and T-686, and inhibitors of α-2-antiplasmin such as anti-α-2-antiplasmin antibody, prostacyclin mimetics.

The inventive compounds may also be useful in combination with other anticancer strategies and chemotherapies such as taxol and/or cisplatin. The compounds may be used in conjunction with anti-tumor agents such as paclitaxel, adriamycin, epithilones, cisplatin, and carboplatin.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to allow for increased efficacy and/or reduced doses of any of the above agents and therefore minimize potential hemorrhagic side-effects.

The compounds of formula I may be administered by any means suitable for the condition to be treated. Systematic treatment is typically preferred for cancerous conditions, although other modes of delivery are contemplated. The compounds may be delivered orally, such as in the form of tablets, capsules, granules, powders, or liquid formulations including syrups; sublingually; bucally; transdermally; parenterally, such as by subcutaneous, intravenous, intramuscular or intrastemal injection or infusion (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CAR-BOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of formula I may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

Assay

Mitochondria were isolated from bovine hearts and purified through a Percoll gradient, sonicated to generate sub mitochondrial particles (SMP), centrifuged, and stored at −80° C. See Gasnier F. et al, *"Use of Percoll Gradients for Isolation of Human Placenta Mitochondria Suitable for Investigating Outer Membrane Proteins,"* Anal. Biochem., Vol 212(1) (1993) at pp. 173–178; and Matsuno-Yagi A et al, *"Studies on the Mechanism of Oxidative Phosphorylation: Effects of Specific $F_O$ Modifiers on Ligand-Induced Conformation Changes of $F_1$,"* Proc. Nat'l Acad. Sci. USA, Vol. 82(22) (1985), at pp. 7550–7554.) ATP hydrolyase activity was determined using SMP and the well-characterized coupled enzyme system in which ATP hydrolysis and subsequent ADP generation is coupled through pyruvate kinase and lactate dehydrogenase to AND+ generation which was monitored by a decrease in absorbance at 340 nm (see Pullman, M. E. et al, *"Partial Resolution of the Enzymes Catalyzing Oxidative Phosphorylation,"* J. Biol. Chem. Vol. 235 (1960), at pp. 3322–3329.) Similarly, compound effects on ATP synthase activity were determined using SMP in the well-characterized coupled enzyme assay in which ATP generation is coupled to NADPH synthesis through the hexokinase and glucose-6-phosphate dehydrogenase pathway (Cross & Kohlbrenner, *"The Mode of Inhibition of Oxidative Phosphorylation by Efrapeptin (A23871). Evidence for an Alternating Site Mechanism for ATP Synthesis,"*

J. Biol. Chem., Vol. 253 (1978) at pp. 4865–4873.) NADPH increase was monitored spectrophotometrically by an increase in absorbance at 340 nm. Compounds were dissolved in 100% dimethyl sulfoxide and tested at increasing concentrations for enzyme inhibition. The concentration of compound causing 50% inhibition of the enzyme ($IC_{50}$) was calculated after the data was fitted using the Levenburg Marquardt algorithm and Microsoft Excel.

Compounds of formula (I), and more particularly, the compounds of Examples 1 through 494 hereof, were tested in this assay and found to have a measurable level of activity for inhibiting $F_1F_0$-ATP hydrolase. Each of the compounds of Examples 1–4 is a non-peptidic small organic compound with less than 1000 molecular weight, with preferred compounds having less than 750 molecular weight.

Abbreviations

The following abbreviations are employed in the Examples and elsewhere herein:
Ph=phenyl
Bn=benzyl
Me=methyl
Et=ethyl
MeOH=methanol
EtOH=ethanol
Pr=propyl
Bu=butyl
AcOH=acetic acid
DBU=1,8-diazabicyclo[5,4,0]undec-7-ene
DIP-Cl=B-chlorodiisopinocampheylborane
DMF=N,N-dimethylformamide
DPPA=Diphenylphosphoryl azide
EDC=N-(3-dimethylaminopropyl)-N'-ethylcarbodiimide
EtOAc=ethyl acetate
$NaBH_4$=sodium borohydride
$NaHCO_3$=sodium bicarbonate
KCNS=potassium isothiocyanate
Pd/C=palladium on carbon
$PtO_2$=platinum oxide
$Ph_3P$=triphenylphosphine
TEA=triethylamine or $Et_3N$
THF=tetrahydrofuran
TFA=trifluoroacetic acid
min=minute(s)
h or hr=hour(s)
L=liter
mL=milliliter
μL=microliter
g=gram(s)
mg=milligram(s)
mol=mole(s)
mmol=millimole(s)
meq=milliequivalent
rt=room temperature
sat or sat'd=saturated
aq.=aqueous
TLC=thin layer chromatography
LC/MS=high performance liquid chromatography/mass spectrometry
MS or Mass Spec=mass spectrometry
mp=melting point Process of Preparation Inventive compounds that are inhibitors of mitochondrial $F_1F_0$ ATP hydrolase may be prepared by methods illustrated in the following Schemes I to II. Starting materials are commercially available or can be readily prepared by one of ordinary skill in the art using known methods. For all of the schemes and compounds, the groups $R^1$–$R^4$ are as described above for a compound of Formula I and X is halogen, unless otherwise indicated. The group "Z" as used in these schemes corresponds to the group $NR_5R_6$, as described for a compound of Formula I, unless indicated otherwise. Groups designated generally as "R" are selected from substituents as set forth in the above definitions.

Solvents, temperatures, pressures, and other reaction conditions may readily be selected by one of ordinary skill in the art. High Speed Analoging (HSA) may be employed in the preparation of compounds, for example, where the intermediates possess a carboxylic acid or amino group. For ease of reference, abbreviations listed above are used in these schemes.

Compounds of Formula I were generally prepared via the following schemes. (Scheme I).

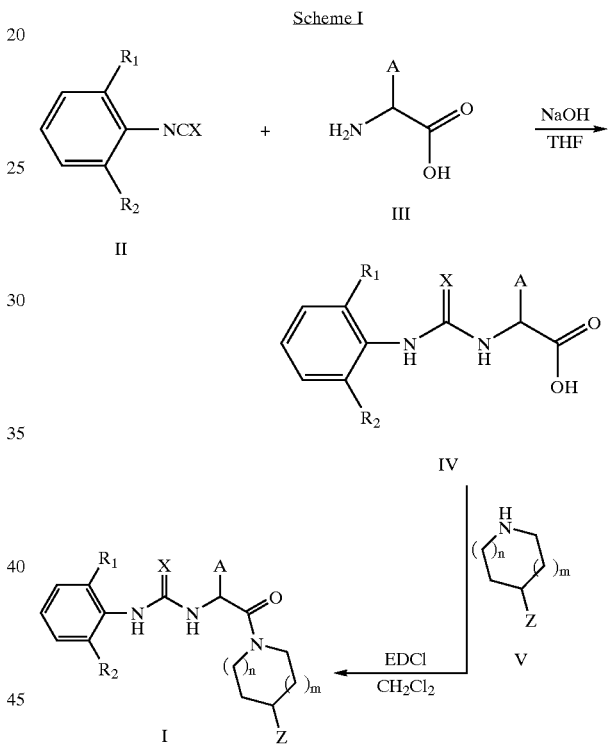

The compounds of formula I can be prepared by the sequential assembly of intermediates of formulas II, III, and V. Intermediates of formulas II, III, and V can be obtained from commercial sources, can be prepared by methods known in the literature, or can readily be prepared by one skilled in the art. Combining an intermediate of formula II and an alpha amino acid intermediate of formula III in the presence of a suitable base such as NaOH leads to an intermediate of formula IV. Treatment of an intermediate of formula IV with a compound of formula V under standard peptide coupling conditions, such as for example, EDCI in $CH_2Cl_2$, provides a compound of formula I.

The invention will now be further described by the following working examples, which are preferred embodiments of the invention.

General Experimental Procedures

All temperatures are in degrees Celsius (°C.) unless otherwise indicated. These examples are illustrative rather than limiting.

EXAMPLE 1

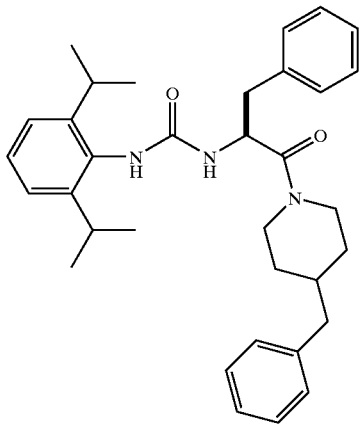

(1S)-1-[1-Benzyl-2-(4-benzylpiperidin-1-yl)-2-oxo-ethyl]-3-(2,6-diisopropylphenyl)-urea General Method A:

To a 25-mL round-bottomed flask containing (L)-phenylalanine (0.50 g, 3.03 mmol) in 5 mL water and 2 mL THF at rt was added 1 mL 1N NaOH, followed by 2,6-diisopropylphenylisocyanate (647 μL, 3.03 mmol, 1.00 equiv), and the mixture was allowed to stir 2.5 h. The reaction mixture was en acidified by the addition of 1M aqueous $NaHSO_4$, and the product precipitated out as a white solid. The product was filtered, washing with water, and air-dried, giving 1.10 g (98%) of the desired urea product as a white solid.

The urea product thus obtained was determined to be of greater than 99% purity as judged by LC/MS, and was carried on to the next step without further purification. To a 25-mL round-bottomed flask containing (1S)-1-[1-benzyl-2-oxo-ethyl]-3-(2,6-diisopropylphenyl)urea (0.50 g, 1.36 mmol) in 5 mL $CH_2Cl_2$ at rt was added 4-benzylpiperidine (240 μL, 1.36 mmol, 100 equiv), followed by 1-[3-(dimethylamino)propyl]-3-ethylcarbodiimide hydrochloride (EDCI, WSC) (261 mg, 1.36 mmol, 1.00 equiv), and the mixture was stirred 4–6 h. The reaction mixture was then diluted with 20 mL $CH_2Cl_2$, and washed successively with with saturated $NaHCO_3$ and brine, dried ($Na_2SO_4$), and concentrated under diminished pressure to give 702 mg (98%) of the desired amide as a white solid. MS: 526 $[M+H]^+$

EXAMPLE 2

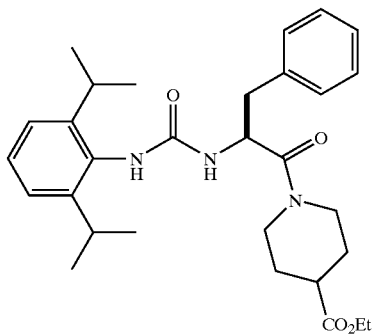

(1S)-1-[1-Benzyl-2-(4-ethoxycarbonylpiperidin-1-yl)-2-oxo-ethyl]-3-(2,6-diisopropylphenyl)-urea This compound was prepared in two steps from 2,6-diisopropylphenylisocyanate, (L)-phenylalanine, and 4-ethoxycarbonylpiperidine in the manner previously described in General Procedure A to give the desired urea amide product as a white solid. MS: 508 $[M+H]^+$

EXAMPLE 3

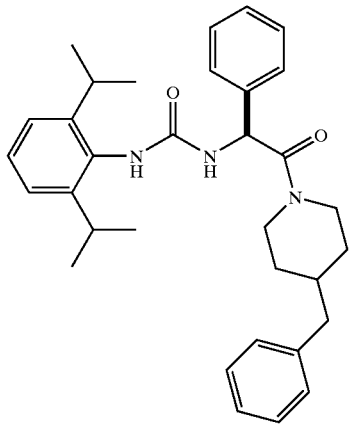

(1S)-1-[1-Phenyl-2-(4-benzylpiperidin-1-yl)-2-oxo-ethyl]-3-(2,6-diisopropylphenyl)-urea This compound was prepared in two steps from 2,6-diisopropylphenylisocyanate, (L)-phenylglycine, and 4-benzylpiperidine in the manner previously described in General Procedure A to give the desired urea amide product as a white solid. MS: 512 $[M+H]^+$

EXAMPLE 4

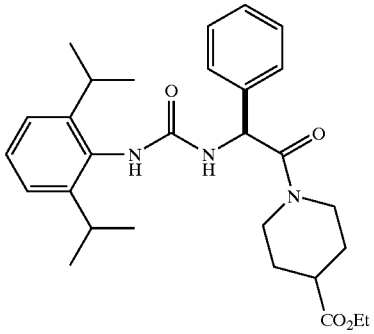

(1S)-1-[1-Phenyl-2-(4-ethoxycarbonylpiperidin-1-yl)-2-oxo-ethyl]-3-(2,6-diisopropylphenyl)-urea This compound was prepared in two steps from 2,6-diisopropylphenylisocyanate, (L)-phenylglycine, and 4-ethoxycarbonylpiperidine in the manner previously described in General Procedure A to give the desired urea amide product as a white solid. MS: 494 $[M+H]^+$

What is claimed is:

1. A method of treating a mitochondrial $F_1F_0$ ATP hydrolase associated disorder selected from myocardial infarction; ventricular hypertrophy; coronary artery disease; non-Q wave MI; congestive heart failure; cardiac arrhythmias; unstable angina; chronic stable angina; Prinzmetal's angina; high blood pressure; intermittent claudication; peripheral occlusive arterial disease; thrombotic or thromboembolic symptoms of thromboembolic stroke; venous thrombosis; arterial thrombosis; cerebral thrombosis; pulmonary embolism; cerebral embolism; thrombophilia; disseminated intravascular coagulation; restenosis; atrial fibrillation; ventricular enlargement; atherosclerotic vascular disease; atherosclerotic plague rupture; atherosclerotic plague formation; transplant atherosclerosis; vascular remodeling atherosclerosis; cancers having tumor cells that do not exhibit the Warburg effect; inflammation; systematic infection; thromboembolic complications of surgery, artificial surfaces, interventional cardiology, immobility, medication, pregnancy and/or fetal loss; and diabetic complications comprising retinopathy, nephropathy and neuropathy in a mammal comprising administering to the patient in need of such treatment an effective amount of at least one compound having the formula (I):

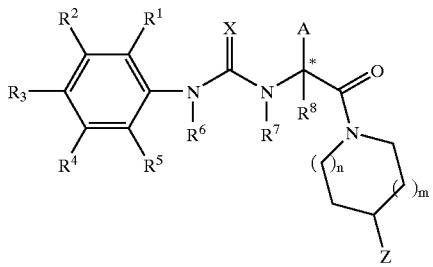

(I)

their enantiomers, diastereomers, and pharmaceutically acceptable salts, prodrugs and solvates thereof, wherein:

X is selected from O or S;

A is selected from hydrogen, alkyl, substituted alkyl, cycloalkyl, heterocycle, aryl, and heteroaryl;

n and m are 0, 1, or 2

$R^1$ through $R^5$ are independently selected from hydrogen, halogen, $NO_2$, CN, $C_{1-8}$alkyl, substituted $C_{1-8}$alkyl, $C_{3-8}$cycloalkyl, aryl, heterocyclo, heteroaryl, $OR^9$, $SR^9$, $COR^{11}$, $CO_2R^{11}$, $CONR^9R^{10}$ or $NR^9R^{10}$;

$R^6$ and $R^7$ are independently hydrogen, alkyl or substituted alkyl;

$R^8$ is hydrogen; $C_{1-8}$alkyl, substituted $C_{1-8}$alkyl, aryl, heterocyclo or heteroaryl;

Z is hydrogen, alkyl, substituted alkyl, cycloalkyl, aryl, heterocyclo, heteroaryl, $COR^{11}$, $CO_2R^{11}$, $SO_2R^{11}$, $S(O)R^{11}$ or $CONR^9R^{10}$;

$R^9$ and $R^{10}$ are independently hydrogen, $C_{1-8}$alkyl, substituted $C_{1-8}$alkyl, $C_{3-10}$cycloalkyl, aryl, heterocyclo, heteroaryl, $COR^{13}$, $SO_2R^{13}$ or $S(O)R^{13}$; and $R^{11}$, $R^{12}$ and $R^{13}$ are independently hydrogen, $C_{1-8}$alkyl, substituted $C_{1-8}$alkyl, $C_{3-10}$cycloalkyl, aryl, heterocyclo or heteroaryl;

wherein each occurrence of $R^9$–$R^{13}$ is chosen independently.

2. The method of claim 1 wherein n and m are both 1.

3. The method of claim 1 wherein $R^2$, $R^3$ and $R^4$ are all hydrogen.

4. The method of claim 1 wherein $R^6$ and $R^7$ are both hydrogen.

5. The method of claim 1 wherein $R^1$ and $R^5$ are independently $C_{1-8}$alkyl.

6. The method of claim 5 wherein $R^1$ and $R^5$ are both isopropyl.

7. The method of claim 1 wherein

Z is $C_{1-8}$alkyl, $C_{2-8}$alkenyl, $C_{1-8}$haloalkyl, cycloalkyl, aryl, arylalkyl, heteroaryl, heteroarylalkyl —$COR^{11}$, —$CO_2R^{11}$, —$SO_2R^{11}$, —$S(O)R^{11}$ or —$CONR^9R^{10}$;

$R^9$ is hydrogen, $R^{10}$ is $C_{1-8}$alkyl or $C_{3-10}$cycloalkyl; aryl or arylalkyl; and $R^{11}$ is hydrogen, $C_{1-8}$alkyl, $C_{3-10}$cycloalkyl, $C_{3-10}$heterocycloalkyl, $C_{3-10}$aryl or $C_{3-10}$arylalkyl.

8. The method of claim 7 wherein Z is benzyl, —$C(O)_2H$, or —$C(O)_2C_1$–$C_8$alkyl.

9. The method of claim 1 wherein:

A is hydrogen, $C_{1-8}$alkyl, heteroaryl, aryl, or alkyl substituted with heterocyclo, aryl, OH, SH, $ST^1$, —$C(O)_tH$, $T^3$-$NT^5T^6$, -$T^8$-$C(O)_tT^9$-$NT^5T^6$ or $T^3$-$N(T^2)T^4NT^5T^6$;

$T^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^2$ and $T^3$ are each independently a single bond, -$T^8$-S(O)$_t$-$T^9$-, -$T^8$-C(O)-$T^9$-, -$T^{18}$-C(S)-$T^9$-, -$T^8$-O-$T^9$-, -$T^8$-S-$T^9$-, -$T^8$-O—C(O)-$T^9$-, -$T^8$-C(O)$_t T^9$-, -$T^8$-C(=$NT^{10}$)-$T^9$- or -$T^8$-C(O)—C(O)-$T^9$-;

$T^5$, $T^6$, $T^7$, $T^8$ and $T^9$ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$OT^{11}$, —$ST^{11}$, —$C(O)_tH$, —$C(O)_tT^{11}$, —O—$C(O)T^{11}$, $T^8C(O)_tN(T^{12})T^{11}$, —$SO_3H$, —$S(O)_tT^{11}$, $S(O)_tN(T^{12})T^{11}$, -$T^{13}$-$NT^{11}T^{12}$, -$T^{13}$-N($T^{12}$)-$T^4$-$NT^{11}T^{22}$, -$T^{13}$-N($T^{11}$)-$T^{12}$-$T^{11}$ and -$T^{13}$-N($T^{18}$)-$T^{14}$-H; or $T^8$ and $T^9$ are each independently a single bond, alkylene, alkenylene or alkynylene;

$T^{11}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ is halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, —$C(O)_tH$ or —$SO_3H$;

$T^{13}$ and $T^{14}$ are each independently a single bond, —S(O)$_t$—, —C(O)—, —C(S)—, —O—, —S—, —O—C(O)—, —C(O)$_t$—, —C(=$NT^{13}$)- or —C(O)—C(O)—;

wherein each occurrence of $T^1$–$T^{14}$ is chosen independently; and t is 1 or 2.

10. The method of claim 9 wherein A is hydrogen, methyl, —$CH_2(CH_3)_2$, —$(CH_2)_2(CH_3)_2$, —$CH(CH_3)CH_2(CH_3)$, —$(CH_2)OH$, hydroxyethyl, —$(CH_2)_2SCH_3$, —$CH_2SH$, phenyl, —$CH_2$(phenyl), —$CH_2$(p-hydroxyphenyl), —$CH_2$(indole), —$(CH_2)C(O)NH_2$, —$(CH_2)_2C(O)NH_2$, —$(CH_2)_2C(O)OH$, —$CH_2C(O)OH$, —$(CH_2)_4NH_2$, —$(CH_2)_3(=NH)CNH_2$ or —$CH_2$(imidazole).

11. The method of claim 10 wherein A is —$CH(CH_3)CH_2(CH_3)$, phenyl, phenylalkyl or —$CH_2$(2-indole).

12. The method of claim 10 wherein $R^8$ is hydrogen and the configuration about the carbon marked with the * is S.

13. A method of treating a mitochondrial $F_1F_0$ ATP hydrolase associated disorder in a mammal selected from myocardial infarction; ventricular hypertrophy; coronary artery disease; non-Q wave MI; congestive heart failure; cardiac arrhythmias; unstable angina; chronic stable angina; Prinzmetal's angina; high blood pressure; intermittent claudication; peripheral occlusive arterial disease; thrombotic or thromboembolic symptoms of thromboembolic stroke; venous thrombosis; arterial thrombosis; cerebral thrombosis; pulmonary embolism; cerebral embolism; thrombophilia; disseminated intravascular coagulation; restenosis; atrial fibrillation; ventricular enlargement; atherosclerotic vascular disease; atherosclerotic plague rupture; atherosclerotic plague formation; transplant atherosclerosis; vascular remodeling atherosclerosis; cancers having tumor cells that do not exhibit the Warburg effect; inflammation; systematic infection; thromboembolic complications of surgery, artificial surfaces, interventional cardiology, immobility, medication, pregnancy and/or fetal loss; and diabetic complications comprising retinopathy, nephropathy and neuropathy comprising administering to the patient in need of such treatment an effective amount of at least one compound having the formula (II);

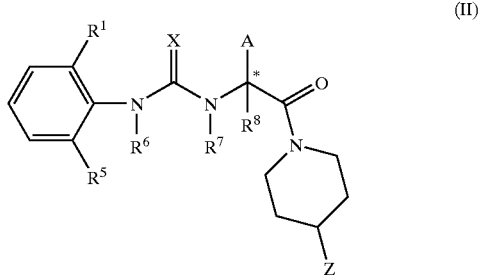

(II)

their enantiomers, diastereomers, and pharmaceutically acceptable salts, prodrugs and solvates thereof, wherein:

A is hydrogen, $C_{1-8}$alkyl, heteroaryl, aryl, or alkyl substituted with heterocyclo, aryl, OH, SH, $ST^1$, —$C(O)_t$H, $T^3$-$NT^5T^6$, -$T^8$-$C(O)_tT^9$-$NT^5T^6$ or $T^3$-$N(T^2)T^4NT^5T^6$;

$R^1$ and $R^5$ are independently $C_{1-8}$alkyl optionally substituted where valence allows;

$R^6$ and $R^7$ are independently hydrogen or $C_{1-8}$alkyl;

$R^8$ is hydrogen, $C_{1-8}$alkyl or substituted $C_{1-8}$alkyl;

Z is hydrogen, $C_{1-8}$alkyl, $C_{2-8}$alkenyl, $C_{1-8}$haloalkyl, cycloalkyl, aryl, arylalkyl, heteroaryl, heteroarylalkyl —$COR^{11}$, —$CO_2R^{11}$, —$SO_2R^{11}$, —$S(O)R^{11}$ or —$CONR^9R^{10}$;

$R^9$ is hydrogen, $R^{10}$ is $C_{1-8}$alkyl or $C_{3-10}$cycloalkyl; aryl or arylalkyl;

$R^{11}$ is hydrogen, $C_{1-8}$alkyl, $C_{3-10}$cycloalkyl, $C_{3-10}$heterocycloalkyl, $C_{3-10}$aryl or $C_{3-10}$arylalkyl;

$T^1$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^2$ and $T^3$ are each independently a single bond, -$T^8$-S(O)$_t$-$T^9$-, -$T^8$-C(O)-$T^9$-, -$T^{18}$-C(S)-$T^9$-, -$T^8$-O-$T^9$-, -$T^8$-S-$T^9$-, -$T^8$-O—C(O)-$T^9$-, -$T^8$-C(O)$_t$$T^9$-, -$T^8$-C(=$NT^{10}$)-$T^9$- or -$T^8$-C(O)—C(O)-$T^9$-;

$T^5$, $T^6$, $T^7$, $T^8$ and $T^9$ are independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alky, each group optionally substituted where valence allows by one to three groups selected from halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$OT^{11}$, —$ST^{11}$, —$C(O)_tH$, —$C(O)_tT^{11}$, —O—$C(O)T^{11}$, $T^8C(O)_tN(T^{12})T^{11}$, —$SO_3H$, —$S(O)_tT^{11}$, $S(O)_tN(T^{12})T^{11}$, -$T^{13}$-$NT^{11}T^{12}$, -$T^{13}$-N($T^{12}$)-$T^4$-$NT^{11}T^{22}$, -$T^{13}$-N($T^{11}$)-$T^{12}$-$T^{11}$ and -$T^{13}$-N($T^{18}$)-$T^{14}$-H; or $T^8$ and $T^9$ are each independently a single bond, alkylene, alkenylene or alkynylene;

$T^{11}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ is halo, cyano, nitro, OH, oxo, —SH, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl or (heteroaryl)alkyl, —$C(O)_tH$ or —$SO_3H$;

$T^{13}$ and $T^{14}$ are each independently a single bond, —$S(O)_t$—, —$C(O)$—, —$C(S)$—, —$O$—, —$S$—, —$O$—$C(O)$—, —$C(O)_t$—, —$C(=NT^{13})$- or —$C(O)$—$C(O)$—; and t is 1 or 2.

14. The method of claim 13 wherein A is hydrogen, methyl, —$CH_2(CH_3)_2$, —$(CH_2)_2(CH_3)_2$, —$CH(CH_3)CH_2(CH_3)$, —$(CH_2)OH$, hydroxyethyl, —$(CH_2)_2SCH_3$, —$CH_2SH$, phenyl, —$CH_2$(phenyl), —$CH_2$(p-hydroxyphenyl), —$CH_2$(indole), —$(CH_2)C(O)NH_2$, —$(CH_2)_2C(O)NH_2$, —$(CH_2)_2C(O)OH$, —$CH_2C(O)OH$, —$(CH_2)_4NH_2$, —$(CH_2)_3(=NH)CNH_2$ or —$CH_2$(imidazole).

15. The method of claim 14 wherein A is —$CH(CH_3)CH_2(CH_3)$, phenyl, $CH_2$(phenyl) or —$CH_2$(2-indole).

16. The method of claim 14 wherein $R^8$ is hydrogen and the configuration about the carbon marked with the * is S.

17. The method of claim 13 wherein $R^1$ and $R^5$ are both isopropyl.

18. The method of claim 13 wherein $R^6$ $R^7$ and $R^9$ are all hydrogen.

19. The method of claim 13 wherein Z is $CH_2$(phenyl), —$C(O)_2H$, or —$C(O)_2C_1$-$C_8$alkyl.

20. The method of claim 1 comprising administering to the patient in need of such treatment an effective amount of at least one compound having the formula:

i. (1S)-1-[1-Benzyl-2-(4-benzylpiperidin-1-yl)-2-oxo-ethyl]-3-(2,6-diisopropylphenyl)-urea;
(1S)-1-[1-Benzyl-2-(4-ethoxycarbonylpiperidin-1-yl)-2-oxo-ethyl]-3-(2,6-diisopropylphenyl)-urea:
(1S)-1-[1-Phenyl-2-(4-benzylpiperidin-1-yl)-2-oxo-ethyl]-3-(2,6-diisopropylphenyl)-urea; or
(1S)-1-[1-Phenyl-2-(4-ethoxycarbonylpiperidin-1-yl)-2-oxo-ethyl]-3-(2,6-diisopropylphenyl)-urea; or ii. a pharmaceutically acceptable salt, prodrug or solvate thereof.

21. The method according to claims 1 or 13 wherein the $F_1F_0$ ATP hydrolase associated disorder is an acute coronary syndrome selected from myocardial infarction, congestive heart failure, and cardiac arrhythmias.

* * * * *